United States Patent [19]
Clark et al.

[11] Patent Number: 5,198,422
[45] Date of Patent: Mar. 30, 1993

[54] STABILIZED SOMATOTROPIN FOR PARENTERAL ADMINISTRATION

[75] Inventors: Michael T. Clark; Robert J. Gyurik, both of Downingtown; Sharon K. Lewis, Conshohocken; Marianne C. Murray, Malvern; Matthew J. Raymond, St. Davids, all of Pa.

[73] Assignee: SmithKline Beecham Corporation, Philadelphia, Pa.

[21] Appl. No.: 896,958

[22] Filed: Jun. 11, 1992

[51] Int. Cl.$^5$ ............................ A61K 37/02; C07K 7/10
[52] U.S. Cl. ............................................ 514/12; 514/2; 514/21; 530/338; 530/345; 530/399
[58] Field of Search ............... 514/2, 12, 21; 530/338, 530/345, 399

[56] References Cited

U.S. PATENT DOCUMENTS 5,015,627  5/1991  Lindsey et al. .................. 514/12

FOREIGN PATENT DOCUMENTS

79950/87  4/1988  Australia .

Primary Examiner—Lester L. Lee
Attorney, Agent, or Firm—Herbert H. Jervis; Joseph A. Marlino; Edward T. Lentz

[57] ABSTRACT

A stabilized complex comprising a growth hormone and an aromatic aldehyde. Specifically, the complex comprises porcine somatotropin and a substituted benzaldehyde and to a method of providing a prolonged release of the somatotropin and improved feed efficiency in animals.

13 Claims, No Drawings

STABILIZED SOMATOTROPIN FOR PARENTERAL ADMINISTRATION

FIELD OF THE INVENTION

This invention relates to a complex comprising a growth hormone (also referred to as a somatotropin) and an aromatic aldehyde. More specifically, this invention relates to a porcine somatotropin (PST)-aromatic aldehyde complex and to a method of producing stable PST compositions resulting in improved feed efficiency in the swine and a prolonged release of the PST.

BACKGROUND OF THE INVENTION

When porcine somatotropin (PST) is administered to pigs on a daily basis a marked improvement in feed efficiency, i.e., feed-to-gain, the animal takes in less food than control animals while gaining weight at the same or greater level. However, it is inconvenient to administer drugs to the swine on a daily basis because of the large expense and amount of time required to deliver the drug to each member of a large group of animals. It would, therefore, be more feasible to apply a single dose and have the PST release over a prolonged period of time. It would appear the easiest way to administer PST would be in a feed, however, like most proteins and macromolecular drugs, PST is not orally bioavailable. In general, the literature has not shown significant ability to deliver proteins and peptides via the oral route. The use of salicylates and mineral oil to enhance oral delivery of these drugs is disclosed in E.P. Application No. 0177342. U.S. Pat. No. 4,548,922, further discloses the use of steroid enhancers, such as fusidic acid.

Parenteral administration, for example, implants have been employed with other macromolecular drugs to give a prolonged release as disclosed in U.S. Pat. No. 4,666,704. PST is an unstable protein susceptible to enzymatic, as well as aqueous degradation. It reacts with itself and is readily cleaved by proteases. Indeed, the instability of the PST implant is thought to be due to the proteases that are generated at the implantation site because of the inflammatory response that takes place (U.S. Pat. No. 5,015,627). It is because of this instability that the administration of PST to swine has hitherto been only marginally, if at all successful. (See for example: U.S. Pat. Nos. 4,837,381; 4,857,505; 5,045,312, and EP Applications 0193917 and 0458064)

There is a commercial need for improved prolonged release implants for parenteral administration of macromolecular drugs having growth hormone activity.

It is, therefore, an object of this invention to provide a composition and method for stabilizing and releasing a biological active growth hormone in animals over a prolonged period of time.

It is a further object of this invention to provide a stable form of PST which will release in swine over a prolonged period of time and which results in improved bioavailability and feed efficiency.

DESCRIPTION OF INVENTION

In accordance with this invention, it has been discovered that when PST is reacted with an aromatic aldehyde a complex is formed which results in improved feed efficiency, i.e., weight gain and feed-to-gain ratio for the animals. The new complex not only has the same bioactivity as PST, but also provides efficacy over a sustained period similar to daily injections of PST.

As mentioned above, several attempts were made to prepare a PST product which would overcome the above noted disadvantages and could be successfully administered to swine. For example, U.S. Pat. No. 5,015,627 discloses PST and leupeptin a tripeptide aldehyde mixed as dry powders, granulated and implants formed from the granulation. These implants were not efficacious.

Unexpectedly, it was discovered that when PST and an aromatic aldehyde of this invention were dissolved in water and the complex was isolated from the solution, a crystalline product resulted which provided a prolonged release of the somatotropin. The complex may be isolated from the aqueous solution by any method well known to the art, such as, for example, concentration, evaporation or lyophilization. Implants prepared from the complex and administered to pigs resulted in a sustained plasma PST level of up to seven days.

The aromatic aldehydes which are present in the complex and employed in the methods of this invention are preferably represented by the following formula

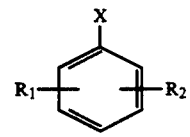

Formula 1 wherein X is CHO or $CH_2CHO$ and each of $R_1$ and $R_2$ can be hydrogen, hydroxy, methoxy, ethoxy, methyl or ethyl.

Preferred aromatic aldehydes present in the complex and method of this invention are compounds of Formula 1 in which X is CHO and each of $R_1$ and $R_2$ is hydroxy or methoxy. A particularly preferred aromatic aldehyde present in the complex and method of this invention is 2 hydroxy-3-methoxy benzaldehyde. This aldehyde is also known as ovanillin.

The aromatic aldehydes which are employed to prepare the stable PST complex of this invention and their method of preparation is well known to the art.

In a preferred embodiment the complex of the invention also comprises an animal growth hormone, such as, for example, human, bovine, avian, porcine, equine or ovine. Advantageously the complex and methods are applicable to porcine somatotropin.

Most advantageously the complex of this invention comprises 2-hydroxy-3-methoxy benzaldeyde and porcine somatotropin.

The aromatic aldehyde of Formula 1 may be present in the complex from about 0.5% to about 10% by weight. Preferably, the aromatic aldehyde may be present from about 0.5% to about 5.0% by weight.

The aromatic aldehyde of Formula 1 and PST complexes of this invention were prepared as follows:

EXAMPLE 1

| Porcine Somatotropin | 99% w/w |
|---|---|
| Aromatic Aldehyde of Formula 1 | 1.0% w/w |

The PST and the aldehyde were dissolved in water, and reacted at 39° C. for 6 to 24 hours. The water is slowly driven off and the resulting product is suspended in ethanol. The suspension is filtered and the precipitate dried overnight in a vacuum oven resulting in dried crystals.

The cystalline complex are formed into 35 mg pellets (implants) with a 3/16 inch punch and die and pressed to about 500 PSI.

EXAMPLE 2

| Porcine Somatotropin | 99.0% w/w |
|---|---|
| 2-Hydroxy-3-Methoxy benzaldehyde | 1.0% w/w |

The complex and implants were prepared following the procedure of Example 1.

EXAMPLE 3

| Porcine Somatotropin | 99.0% w/w |
|---|---|
| 4-Hydroxy-3-Methoxy benzaldehyde | 1.0% w/w |

EXAMPLE 4

| Porcine Somatotropin | 99.0% w/w |
|---|---|
| 4-Methoxy benzaldehyde | 1.0% w/w |

The above complexes were prepared following the procedure of Example 1.

The shape of the pellets or implants is not critical and any configuration suitable for implantation may be employed. In addition to the somatotropin and the aromatic aldehyde, it may be advantageous to include other pharmaceutical excipients in the compositions of this invention. For example, the implant may contain lubricants, such as, magnesium stearate or stearic acid, fillers, such as, sucrose or lactose and binders, such as, acacia, polyvinylpyrrolidone or gelatin.

The compositions of this invention may be administered to an animal parenterally employing any of the known implantation methods, such as subcutaneous, intramuscular and intraperitoneal. Preferably, the implant composition is subcutaneously implanted in an animal employing any well known technique.

Animals which are treated in this manner may include, without limitations, mammals such as cattle, sheep, goats, swine and the like, and birds such as poultry.

The following procedure was employed to determine plasma PST levels, feed consumption, average daily gain and feed-to-gain.

Pigs were housed in a barn and acclimated 3–4 weeks to pens containing 7–8 pigs per pen. Within each pen, pigs had access to a heated shelter and on ad libitum feed and water.

When most of the pigs reached approximately 75 kg, their weights were statistically compared and alloted to 4 different treatments, 9 pigs per treatment. The starting day was considered day 0, on which body weights, control blood samples, and implants were initiated. At the end of 21 days, the pigs were removed from the study.

The pigs were injected with 1 pellet (depending on treatment) S.C. behind the ear a commercial livestock implant gun was used and the site of administration was swabbed with 70% ETOH. Pigs treated daily at 5 mg/head/day were injected with a 1½ inch 16 g needle in the neck area. Treatment was as follows:

1. Control—sham implant
2. PST—daily injection—(5 mg/head/day)
3. PST—o-vanillin implant—1 pellet (35 mg PST)
4. PST—leupeptin implant—1 pellet (35 mg PST).

Blood samples were drawn from the snared pig via jugular vein, using a vacutainer with a 1½ inch needle. The blood was allowed to clot, centrifuged, and plasma removed. The plasma samples were frozen for PST determinations which were assayed at a later date.

FEED CONSUMPTION

All pigs received Enhanced Finisher diet #634 throughout the study. On day zero, two bags of feed were added to feeder and an initial weight taken. The feeders were checked daily and a bag of preweighed feed was added as needed (feeders were never allowed to empty). A final weight of feeder was taken on the day all pigs were removed from a pen. The final weight was subtracted from initial weight and this was added to total feed added which equals Total Feed Consumption per pen.

|   | Initial weight of feeder |
|---|---|
| − | Final weight of feeder |
|   | Total |
| + | Total weight of bags of feed added |
|   | Total feed consumption per pen. |

The pigs were weighed in kilograms individually on day zero and at seven day intervals throughout the study. Overall Average Daily Gain was derived by substracting the initial weight on day zero from the pigs final weight and dividing by the number of days on study.

Feed-to-Gain per pen during the study was derived by adding all feed consumed per pen and dividing by total weight gain per pen.

The Average Daily Gain (ADG) and Feed-to-Gain results are presented in the following Table:

TABLE 1

| PST Treatment | Average Daily Gain, Kg | % Increase over Control | Feed to Gain Ratio | % of Control |
|---|---|---|---|---|
| Control (no PST) | 0.71 | — | 4.4 | — |
| 5 mg/head/day | 0.86 | 21 | 2.7 | 39 |
| o-vanillin/PST (1 pellet) (35 mg) | 0.79 | 11.9 | 3.52 | 21 |
| leupeptin/pST (1 pellet) (35 mg) | 0.70 | −1.4 | 4.12 | 6 |

The results of the plasma PST levels indicate that the daily injection of PST demonstrates very little, if any, plasma PST levels after 24 hours. In contrast, after implantation of the pellets of this invention, a sustained plasma PST level was noted.

The above results clearly indicate when the o-vanillin/PST complex is administered to pigs by implantation, there is an increase over the control in both the average daily gain and feed-to-gain observed in the pigs.

Furthermore, the results indicate that it is not necessary to add a protease inhibitor with the PST. We show now that a non-protease inhibitor (o-vanillin) interacts in a positive manner with PST to maintain efficacy over a 21 day period.

The method in accordance with this invention comprises parenterally administering to an animal organism the above PST-aromatic aldehyde complex in an amount sufficient to prolong PST blood levels and enhance feed efficiency. The dose is dependent on several factors, for example, the size of the animal and the effect desired. For administration to swine, the complex, preferable, will be in an amount of from 10 mg. to about 500 mg, advantageously from about 30 mg to about 75 mg equal doses will be administered at intervals of about 7 to 42 days.

What is claimed is:

1. A method for providing a prolonged release of a somatotropin which comprises parenterally administering to an animal organism in an amount sufficient to produce said release a growth promoting agent being a complex of a somatotropin and an aromatic aldehyde having the following formula:

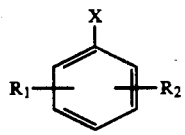

in which X is CHO or $CH_2CHO$ and each of $R_1$ and $R_2$ is hydrogen, hydroxy, methoxy, ethoxy, methyl or ethyl in which the aromatic aldehyde is present in the complex in an amount of from about 0.5% to about 10% by weight.

2. The method of claim 1 in which X is CHO and each of $R_1$ and $R_2$ is hydroxy or methoxy and the somatotropin is selected from the group consisting of porcine, human, bovine, avian, equine and ovine.

3. The method of claim 2 in which the aldehyde is 2-hydroxy-3-methoxy benzaldehyde and the somatotropin is porcine somatotropin.

4. The method of claim 1 in which the complex is administered in an amount of from about 10 mg to about 500 mg.

5. The method of claim 4 in which the administration is done at from about 7 to 42 day intervals.

6. The method of claim 1 in which the complex is administered subcutaneously as an implant.

7. A growth promoting complex which produces a prolonged release of a somatotropin which comprises a somatotropin and an aromatic aldehyde having the following formula:

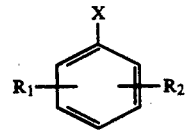

in which X is CHO or CH2CHO and each of R1 is hydrogen, hydroxy, hydroxy, methoxy, ethoxy, methyl or ethyl in which the aromatic aldehyde is present in the complex in an amount of from about 0.5% to about 10% by weight.

8. The complex of claim 7 in which X is CHO and each of $R_1$ and $R_2$ is hydroxy or methoxy and the somatotropin is selected from the group consisting of porcine, human, bovine, avian, equine and ovine.

9. The complex of claim 8 in which the aldehyde is 2-hydroxy-3-methoxy benzaldehyde and the somatotropin is porcine somatotropin.

10. A method for improving feed efficiency in animals which comprises administering to an animal organism in an amount sufficient to produce said efficiency the complex of claim 7.

11. The method of claim 10 in which the complex is porcine somatotropin and 2-hydroxy-3-methoxy benzaldehyde.

12. The method of claim 10 in which the complex is administered in an amount of from about 10 mg to about 500 mg.

13. The method of claim 12 in which the administration is done from about 7 to about 42 day intervals.

* * * * *